United States Patent [19]

Machida et al.

[11] Patent Number: Plant 7,758

[45] Date of Patent: Dec. 31, 1991

[54] JAPANESE PEAR TREE "CHIKUSUI"

[75] Inventors: Yutaka Machida, Tsuchiura; Kazuo Kotobuki, Ibaraki; Ichiro Kajiura, Tsukuba; Yoshihiko Sato, Tsukuba; Teruo Kozono, Tsukuba; Kitsuo Kanato, Nagoya; Kanetsugu Seike, Kawasaki; Isao Shimura, Machida; Mitsuo Omura, Shizuoka; Kazuyuki Abe, Tsukuba; Akio Kurihara, Tsuchiura; Osamu Kishimoto, Sakado, all of Japan

[73] Assignee: Fruit Tree Research Station Ministry of Agriculture, Forestry and Fisheries, Tsukuba, Japan

[21] Appl. No.: 494,270

[22] Filed: Mar. 15, 1990

[51] Int. Cl.[5] ..... A01H 5/00

[52] U.S. Cl. ..... Plt./36

[58] Field of Search ..... Plt./36

*Primary Examiner*—James R. Feyrer

*Attorney, Agent, or Firm*—Armstrong, Nikaido, Marmelstein, Kubovcik & Murray

[57] ABSTRACT

Disclosed herein is a Japanese pear tree having a moderate vigor and an easily maintained moderate spur development, a high resistance to black spot disease and a high productivity. This tree produces an oblate-shaped fruit which matures early in the season, i.e., from the start to the middle of August, in the central part of the Kantō district, Japan. The fruit has a medium size and the same weight as 'Kōsui', i.e., 250 to 300 g, a yellowish brown skin, and a white flesh which is soft, crisp and very juicy with a high Brix the pH of the juice being about 5.2, a particular smell without aromatic flavor, giving an excellent dessert quality.

5 Drawing Sheets

BACKGROUND OF THE VARIETY

The present invention relates to a new and distinct variety of Japanese pear tree having a moderate vigor and an easily maintained moderate spur development, is strongly resistant to black spot disease, and has a high productivity.

In Japan, excellent cultivars known as "Sansui" (namely, three cultivars having a Japanese name ending in "sui", respectively, i.e., "Kōsui", Shinsui", and "Hōsui") comprise nearly 50 percent (based on the cultivated area) of the total cultivars of the Japanese pear tree, after they are provided to a producer of pear fruit. However, the cultivation of "Kōsui", among the "Sansui", has greatly increased and, for example, an imbalance between supply and demand has occurred. Thus, desirably, the term of distribution of the pear fruit is extended, using an early and a late cultivar, particularly there is required a useful early cultivar. The "Shinsui", as an early cultivar, has a low productivity and a high acidity, and does not agree with present consumers' tastes.

One purpose of our breeding program is to provide improved varieties of the pear fruit tree which can be substituted for the "Shinsui".

ORIGIN AND ASEXUAL REPRODUCTION OF THE VARIETY

The new variety of Japanese pear tree was a cross-seedling which originated from a crossing between "Hōsui" (♀) (the seed parent) having excellent fruit quality with a yellowish-brown skin, and "Hakkō" (♂) (the pollen parent), which is an early cultivar bearing a fruit having a yellowish-green skin, in 1970 at the Horticultural Research Station of the Ministry of Agriculture, Forestry and Fisheries, residing at Hiratsuka-shi, Kanagawa-ken, Japan was kept in a nursery for a long time, and then was planted in 1976 at the Research Station, residing at Tsukuba-shi, Ibaraki-ken, Japan. The tree bore fruit for the first time in 1978, and both the maturation period and the quality of the fruit corresponded to the above-stated purpose. Accordingly, the tree was selected as the first selection in 1982, and subjected to local adaptability tests from 1983 at 34 of the experimental stations in main pear growing regions, such as Saitama-ken, of Japan, as the strain number "Tsukuba No. 36". As a result, this new variety of Japanese pear tree according to this invention was judged to be a superior new cultivar, and this new variety of Japanese pear tree was named "Chikusui" in 1988. The genus and species of the tree is "*Pyrus pyrifolia* Nakai".

We asexually reproduced this new and distinct variety of Japanese pear tree "Chikusui", by grafting, at the Fruit Tree Research Station, Ministry of Agriculture, Forestry and Fisheries, residing at 2-1 Fujimoto, Tsukuba-shi, Ibaraki-ken, Japan, and confirmed the homogeneity and stability of "Chikusui" according to this invention.

An application for this new variety of Japanese pear tree "Chikusui" under the Seeds and Seedling Law of Japan was filed on Mar. 31, 1988, and was registered on Sept. 19, 1989, under the registration No. 2,060.

SUMMARY OF THE VARIETY

This new variety of Japanese pear tree has a moderate vigor and is not as strong as "Shinsui", a moderate bud generating, a good maintained spur compared with "Kōsui", and a moderate spur development, a high productivity, pollination compatible with "Kōsui" and "Shinsui", an almost the same flowering time as "Kōsui", and is highly resistant to black spot disease. The tree produces an oblate-shaped fruit which matures early in the season, i.e., from the start to the middle of August, in the central part of Kantō district, Japan. The fruit has a medium size and the same weight as "Kōsui", i.e., 250 to 300 g, a yellowish-brown skin, and a white flesh which is soft and crisp. The fruit juice has a high Brix a low acidity at a pH of about 5.2, and the same fruit quality as "Kōsui".

DESCRIPTION OF THE VARIETY

Figure 1:
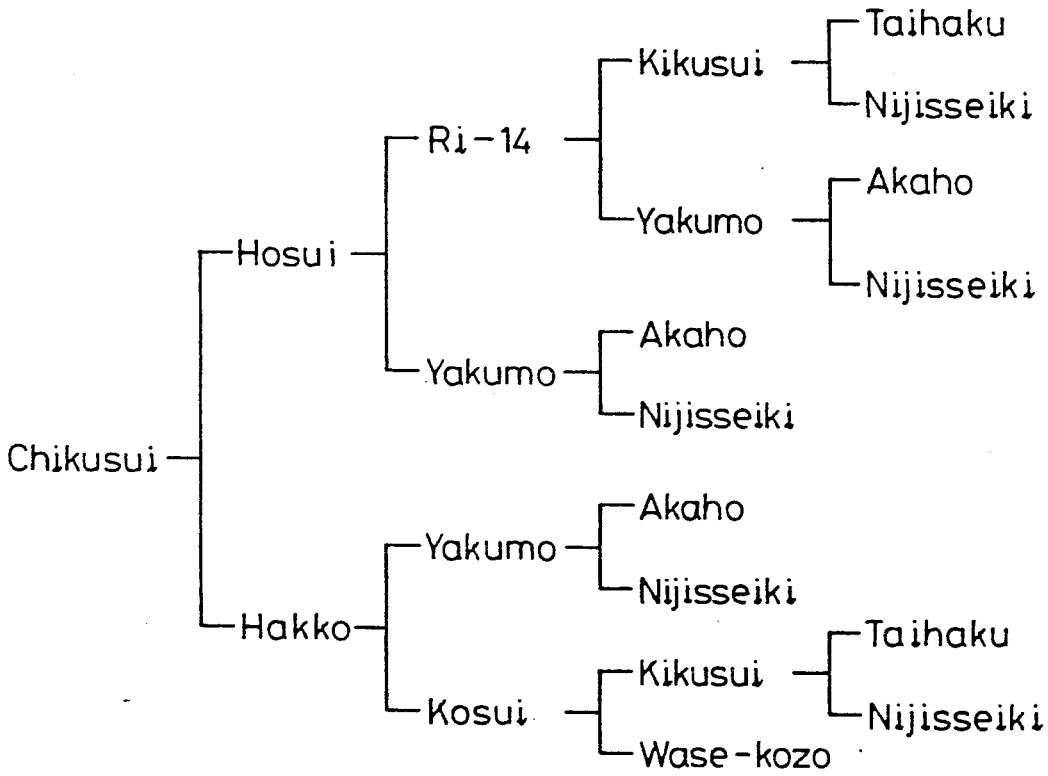
FIG. 1 gives the pedigree of the new and distinct variety of Japanese pear tree "Chikusui"
Figure 2:
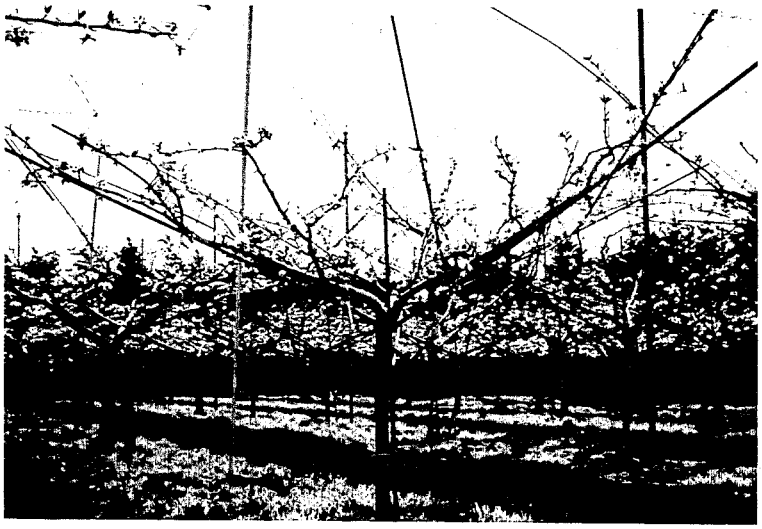
FIG. 2 is a photograph of a shape of the new variety of Japanese pear tree.
Figure 3:
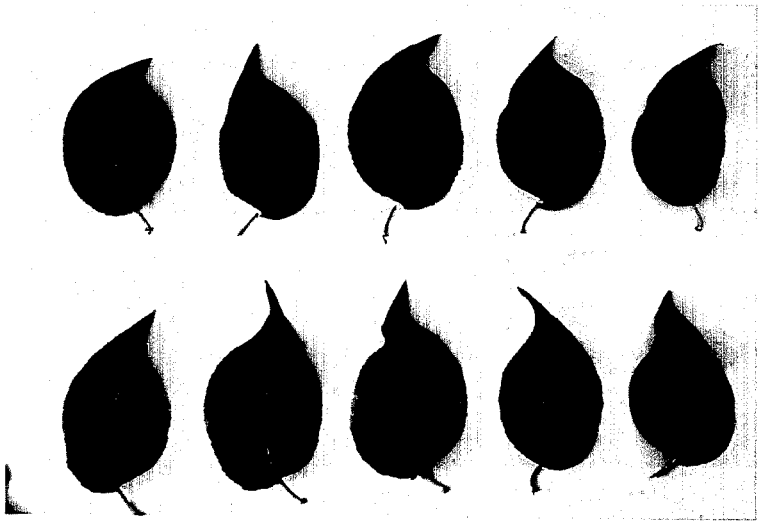
FIG. 3 is a photograph of adult leaves (adaxial) of the new variety of Japanese pear tree.
Figure 4:
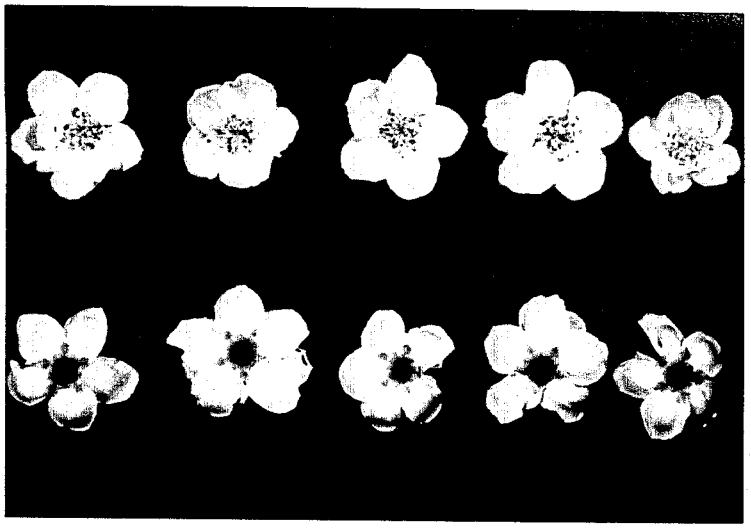
FIG. 4 is a photograph of a flower of the new variety of Japanese pear tree.
Figure 5:
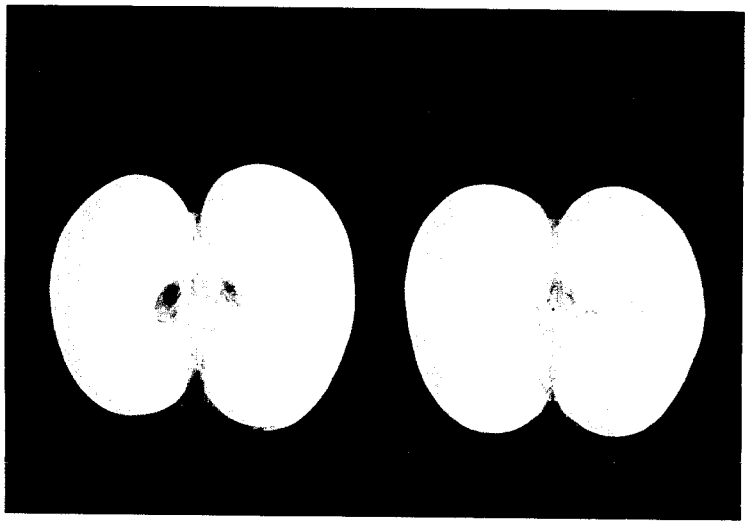
FIG. 5 is a photograph of longitudinal-sectional views of fruit of the new variety of Japanese pear tree.
Figure 6:
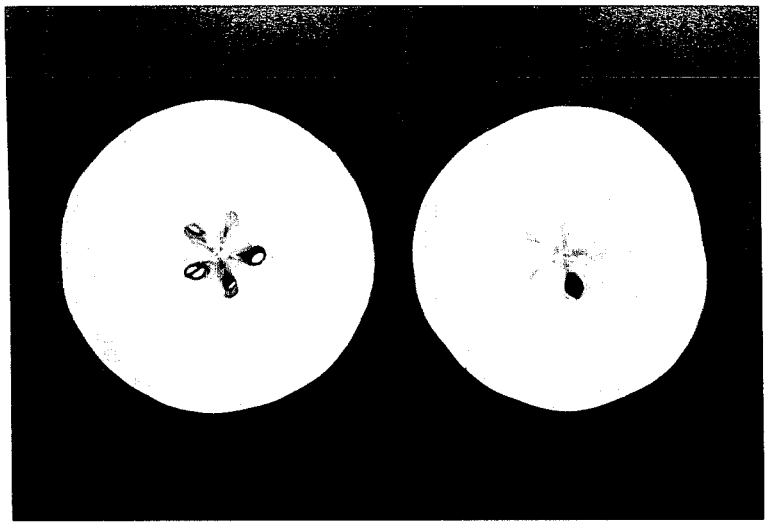
FIG. 6 is a photograph of cross-sectional views of fruit of the new variety of Japanese pear tree.
Figure 7:
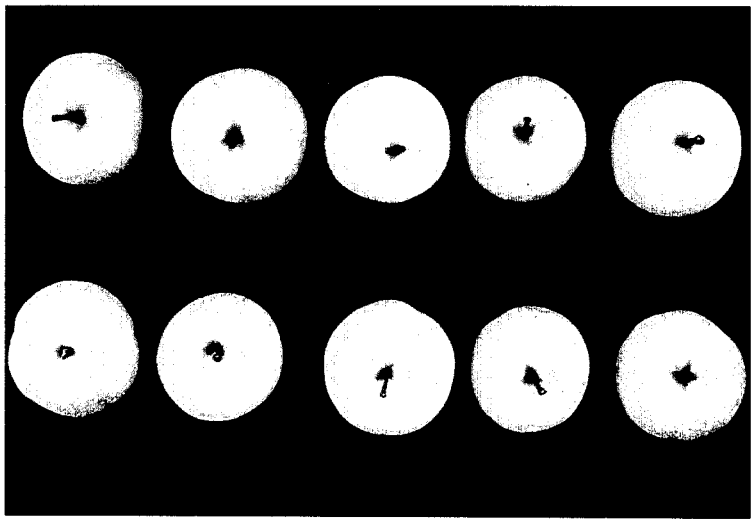
FIG. 7 depicts a group of 10 whole fruit of the variety from the stem end; and, FIG. 8 depicts a group of 10 whole fruit of the variety from the blossom end.
Figure 8:
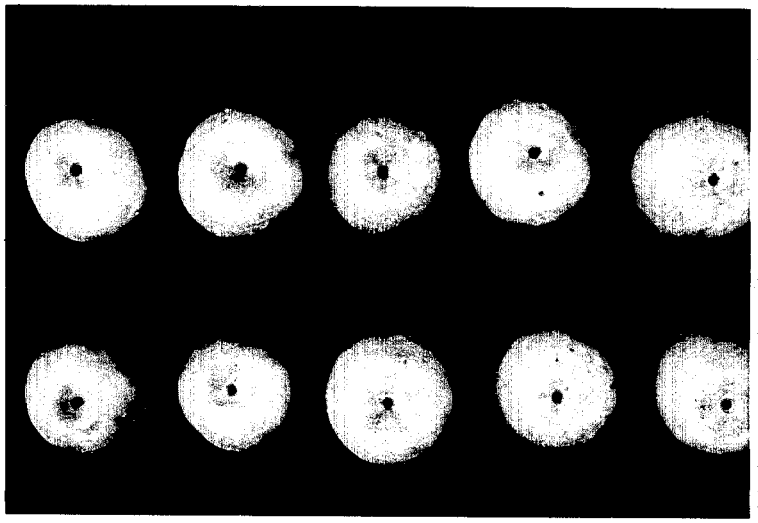

Color values presented are taken from the *Japanese Horticultural Society Color Chart* (J.H.S.C.). Following each such definition, in parenthesis, appear the equivalent color name from the *Inter-Society Color Council-National Bureau of Standards* (ISSC-NBS), and, if an equivalent color is available, the *Royal Horticultural Society Colour Chart* (R.H.S.) color designation. The characteristics of the new and distinct variety of Japanese pear tree "Chikusui" are as follows:

Tree:

*Vigor.*—Medium, not as strong as "Shinsui" and "Nijisseiki". The tree has the same chilling requirements and hardiness, as for the other Japanese pear.

*Spur.*—Bearing moderately, and easier to maintain than "Kōsui". The spur is at least 4 per meter of the tree, and the flower bud is about 1.1 per spur.

*Predominance of axillary flower bud.*—Slight increment beyond medium.

*Time of bud break.*—Medium.

*Production.*—As productive as "Kōsui", judging from the predominance of flower buds, the size of the fruit and the like.

*Cross-compatibility.*—Cross-compatible with, e.g., "Kōsui" and "Shinsui."

Branches:

*Thickness.*—Medium.

*Length of internode.*—Short, 4.8 cm.

*Lenticel.*—Medium, shorter than "Shinsui".

*Color.*—Brown (J.H.S.C. 1309; new bark) (ISCC-NBS strong brown) and grayish-pink (J.H.S.C. 0717; mature bark) (ISCC-NBS light grayish-red; R.H.S. 201C).

*Density of pubescence.*—Low, same as "Kōsui".

Leaves:

*Shape.*—Oval.

*Size.*—Medium, same as "Kōsui". The leaf has a size of about 114 mm in length and about 63 mm in width.

*Color.*—Dark bluish-green (J.H.S.C. 4907) (ISCC-NBS dark green; R.H.S. 131A, 133A).

*Petiole.*—Short.

*Color of petiole.*—Light yellow green (J.H.S.C. 3503) (ISCC-NBS light yellow green; R.H.S. 144D, 145C).

*Young leaves.*—Having green color and low pubescence density.

Flowers:

*Flower number in a flower cluster.*—Medium.

*Size.*—Large.

*Color.*—White, and white at the pit at fat bud.

*Shape of petals.*—Oval and large.

*Color of petals.*—Purplish-white (J.H.S.C. 8601) (ISCC-NBS purplish-white).

*Notch of margin or petal.*—Medium.

*Number of petal.*—Many flowers having five petals.

*Color of anther.*—Red.

*Pollen.*—Fertile.

*Flowering time.*—Late in the season; almost the same time as "Kōsui", about 3 days later than "Shinsui". The length of the peduncle is about 17.2 mm.

Fruit:

*Size.*—About 279 g, larger than "Shinsui" and slightly smaller than "Kōsui".

*Shape.*—Oblate with a medium wide middle stalk cavity and a slightly narrow medium deep calyx end, and a good fruit uniformity.

*Color of peduncle.*—Dull green (J.H.S.C. 4010) (ISCC-NBS moderate yellowish-green; RHS 136C, 139B).

*Color of skin and dot.*—Strong orange (J.H.S.C. 1606) (ISCC-NBS vivid orange) and yellowish-gray (J.H.S.C. 2914) (ISCC-NBS yellowish-gray; RHS 196B), respectively and fruit skin is russet type. The color of the fruit skin is tinged with red on the sunny side, but the color is not based on anthocyanin.

*Calyx perpetual fruit.*—Absent.

*Size of dot.*—Medium.

*Density of dot.*—Medium.

*Color of flesh and core.*—Yellowish-white (J.H.S.C. 3301) (ISCC-NBS yellowish white; RHS 155B).

*Color of seed.*—Dark grayish-purple (J.H.S.C. 8315) (ISCC-NBS dark grayish-purple).

*Flesh.*—Soft, crisp and juicy. The firmness is about 4.8 lbs. according to Magnessteller's hardness meter index; almost the same level as "Kōsui", and slightly higher than "Hōsui".

*Taste.*—Having a high sweetness that is almost the same level as "Kōsui", the sugar content of the fruit juice is about 13%, a low acidity that is substantially the same level as "Kōsui", (the taste of fruit flesh changes as it approaches the core, i.e., the portion nearest to the core has a sourer taste than the main flesh), is very juicy and the pH of the fruit juice is more than 5.0, no astringency, a particular smell without aromatic flavor, which gives an excellent dessert quality.

*Maturity.*—Ripening early in season, about one month earlier than "Hōsui", and a few days earlier than "Hakkō" and "Shinsui", e.g., from the start to mid-August, in the central Kantō district, Japan.

*Size of mature fruit.*—About 81.4 mm in longitudinal section and about 69.2 mm in cross section.

*Seed cells.*—The fruit has 5 seed cells, and each seed cell generally has up to 2 seeds; the total seeds being 5 to 6 per fruit.

*Use.*—Suitable for dessert.

*Keeping quality.*—Can be kept for 5 to 7 days at 25° C.

*Resistance to pests and diseases.*—Has a strong resistance to black spot disease and no occurrence of an attach of the disease to date, and non-sensitive to pear necrotic spot.

*Core breakdown.*—None.

*Watercore.*—None.

*Fruit cracking.*—None.

*Culture.*—The skin of the fruit of the new cultivar "Chikusui" is apt to remain green at the calyx end, and it is difficult to judge the fruit harvesting stage. A peduncle of this new cultivar tree is short, and thus the problems of damaged fruit and snapped stalks arise, but these problems may be solved by an appropriate fruit thinning technique.

The date of the first and peak blooming of the present variety, compared with the dates of pollinator, are as follows:

| | Date of first blooming | Date of peak blooming |
|---|---|---|
| present variety | April 14 | April 16 |

-continued

| | Date of first blooming | Date of peak blooming |
|---|---|---|
| pollinator (Chojuro) | April 11 | April 14 |

(at Tukuba-shi, Ibaraki, Japan).

The new variety of Japanese pear tree is cultivated and kept at my farm located at 2-1 Fujimoto, Tsukuba, 305 Japan.

Since the new variety, the "Chikusui" Japanese pear tree, has a strong resistance to diseases which generally attack pear trees, an excellent dessert quality, and the harvesting stage of the fruit is early in the season, the trees of this variety can be conveniently planted, in place of the excellent Japanese pear tree, "Kosui", in an orchard.

We claim:

1. A new and distinct variety of Japanese pear tree, substantially as illustrated and described herein, characterized over the known Japanese pear trees by having a moderate vigor, a good maintained spur, a strong resistance to black spot disease and no sensitivity to pear necrotic spot disease; having green leaves and young leaves and white flowers; a large amount of fruit which has a yellowish brown skin and an oblate shape; and a flesh which is white in color, soft, crisp and very juicy, with a high sweetness, a low acidity, no astringency, a particular smell without aromatic flavor; and a harvesting stage of the fruit being early in the season.

* * * * *

Fig. 1 Pedigree of 'Chikusui'